US010335218B2

(12) United States Patent
Sweeney (10) Patent No.: US 10,335,218 B2
(45) Date of Patent: Jul. 2, 2019

(54) MULTICHANNEL CANNULA AND METHODS FOR USING SAME

(71) Applicant: Spinal Generations, LLC, Mokena, IL (US)

(72) Inventor: Patrick J. Sweeney, Flossmoor, IL (US)

(73) Assignee: Spinal Generations, LLC, Mokena, IL (US)

( * ) Notice: Subject to any disclaimer, the term of this patent is extended or adjusted under 35 U.S.C. 154(b) by 0 days.

(21) Appl. No.: 15/663,231

(22) Filed: Jul. 28, 2017

(65) Prior Publication Data

US 2017/0325866 A1 Nov. 16, 2017

Related U.S. Application Data (62) Division of application No. 13/679,312, filed on Nov. 16, 2012.

(51) Int. Cl.
*A61B 17/88* (2006.01)
*A61B 17/34* (2006.01)

(52) U.S. Cl.
CPC ...... *A61B 17/8816* (2013.01); *A61B 17/3472* (2013.01); *A61B 2017/3447* (2013.01)

(58) Field of Classification Search
CPC .. A61B 17/3417–3439; A61B 17/3472; A61B 17/8805–8822; A61B 2017/3454; A61M 5/32; A61M 29/00; A61M 37/00; A61M 25/01; A61M 25/09
See application file for complete search history.

(56) References Cited

U.S. PATENT DOCUMENTS

| 4,099,528 A | 7/1978 | Sorenson et al. |
| 5,195,962 A * | 3/1993 | Martin ............... A61M 25/001 604/43 |
| 5,250,055 A * | 10/1993 | Moore ............... A61B 17/0469 128/898 |

(Continued)

FOREIGN PATENT DOCUMENTS

CN 102711670 A 10/2012

OTHER PUBLICATIONS

First Office Action and English Translation for CN Application No. 201380058969.8 dated Oct. 8, 2016, 20 pages.

(Continued)

*Primary Examiner* — Nicholas J Plionis
*Assistant Examiner* — Steven J Cotroneo
(74) *Attorney, Agent, or Firm* — Foley & Lardner LLP (57) ABSTRACT

A method for delivering a substance to bone includes placing a stabilizing wire in a bone, creating a hole in the bone around the stabilizing wire, and providing a multichannel cannula, comprising. The multichannel cannula includes a first channel having an open proximal end and an open distal end, the first channel being configured to receive the stabilizing wire, and a second channel having an inlet portal and an exit portal that are in fluid communication. The method further includes inserting the multichannel cannula into the hole in the bone such that the first channel receives the stabilizing wire, and delivering the substance into the bone by introducing the substance into the inlet portal of the second channel such that the substance exits the second channel through the exit portal.

11 Claims, 5 Drawing Sheets

(56) References Cited

U.S. PATENT DOCUMENTS

| | | | |
|---|---|---|---|
| 5,380,276 A * | 1/1995 | Miller | A61M 1/285 604/264 |
| 5,788,703 A * | 8/1998 | Mittelmeier | A61B 17/8808 606/94 |
| 5,800,439 A * | 9/1998 | Clyburn | A61B 17/8808 606/93 |
| 5,833,652 A * | 11/1998 | Preissman | A61M 25/0029 604/82 |
| 6,004,310 A * | 12/1999 | Bardsley | A61M 25/0009 604/524 |
| 6,146,373 A | 11/2000 | Cragg et al. | |
| 6,179,809 B1 | 1/2001 | Khairkhahan et al. | |
| 6,241,734 B1 * | 6/2001 | Scribner | A61B 17/8816 606/93 |
| 6,395,007 B1 * | 5/2002 | Bhatnagar | A61B 17/8816 606/94 |
| 6,440,141 B1 * | 8/2002 | Philippon | A61B 17/1615 604/60 |
| 6,533,782 B2 | 3/2003 | Howell et al. | |
| 6,629,947 B1 | 10/2003 | Sahatjian et al. | |
| 6,663,596 B2 | 12/2003 | Griego et al. | |
| 6,780,167 B2 * | 8/2004 | Leone | A61M 5/1408 604/173 |
| 6,921,380 B1 | 7/2005 | Epstein et al. | |
| 7,632,294 B2 | 12/2009 | Milbodker et al. | |
| 7,678,098 B2 * | 3/2010 | Bertolero | A61M 25/10 604/4.01 |
| 7,717,956 B2 | 5/2010 | Philipp | |
| 7,901,407 B2 | 3/2011 | Olson et al. | |
| 8,241,245 B2 | 8/2012 | Markel et al. | |
| 8,303,598 B2 | 11/2012 | Frankel et al. | |
| 8,597,301 B2 | 12/2013 | Mitchell | |
| 8,617,585 B2 | 12/2013 | Boden et al. | |
| 8,684,965 B2 * | 4/2014 | Rabiner | A61B 17/7275 604/101.02 |
| 2002/0007130 A1 * | 1/2002 | Burbank | A61B 10/0266 600/564 |
| 2004/0006341 A1 * | 1/2004 | Shaolian | A61B 17/1671 606/86 A |
| 2004/0236340 A1 * | 11/2004 | Cirotteau | A61B 17/7095 606/86 R |
| 2005/0015059 A1 * | 1/2005 | Sweeney | A61B 17/864 604/264 |
| 2005/0080398 A1 * | 4/2005 | Markel | A61M 25/0014 604/508 |
| 2006/0253081 A1 | 11/2006 | Paulos et al. | |
| 2007/0154460 A1 | 7/2007 | Kraft et al. | |
| 2007/0225219 A1 | 9/2007 | Boden et al. | |
| 2009/0088604 A1 | 4/2009 | Lowry et al. | |
| 2009/0204158 A1 | 8/2009 | Sweeney | |
| 2010/0262069 A1 * | 10/2010 | Rabiner | A61B 17/7097 604/21 |
| 2011/0082441 A1 * | 4/2011 | Allee | A61B 10/025 604/506 |
| 2011/0224494 A1 | 9/2011 | Piskun et al. | |
| 2011/0224741 A1 | 9/2011 | Forrest | |
| 2012/0041395 A1 | 2/2012 | Sweeney | |
| 2012/0109102 A1 * | 5/2012 | Vandewalle | A61B 17/3472 604/506 |
| 2012/0221009 A1 * | 8/2012 | Tada | A61B 17/7258 606/93 |
| 2012/0330320 A1 * | 12/2012 | Takizawa | A61B 17/8816 606/94 |
| 2013/0158471 A1 | 6/2013 | Neel et al. | |
| 2014/0142584 A1 | 5/2014 | Sweeney | |
| 2014/0276596 A1 | 9/2014 | Vandewalle | |
| 2015/0094730 A1 * | 4/2015 | Hayakawa | A61B 17/7097 606/93 |

OTHER PUBLICATIONS

International Preliminary Report on Patentability for PCT Application No. PCT/US2014/063906, dated May 26, 2016, 9 pages.

International Search Report and Written Opinion for PCT Application No. PCT/US2013/070384, dated Mar. 20, 2014, 13 pages.

International Search Report and Written Opinion for PCT application No. PCT/US2014/063906, dated Feb. 9, 2015, 13 pages.

* cited by examiner

MULTICHANNEL CANNULA AND METHODS FOR USING SAME

CROSS-REFERENCE TO RELATED PATENT APPLICATIONS

This application is a Divisional application of U.S. application Ser. No. 13/679,312, filed Nov. 16, 2012, which is hereby incorporated by reference herein in its entirely.

BACKGROUND

The present invention relates generally to the field of devices and methods for delivering substances to bone. More particularly, the present invention concerns devices and methods for delivering substances to the interior of fractured or otherwise injured bones, especially to the fracture interface. The present invention further relates to devices and methods for removing material from the interior of a bone.

As techniques for delivering substances to bone progress, there remains an imprecision during substance delivery prior to bone implant placement. A bone implant may be a bone screw, nail, or other device implanted into a bone to stabilize portions of a fractured bone. At least three techniques are currently available to deliver substances to bone. One technique involves delivering the substance into a drilled hole in a fractured bone without fracture stabilization. The lack of fracture stabilization causes difficulties in delivering substances to an intended location using this technique. A second technique includes drilling a separate hole in a bone for the substance to be delivered after implant placement. Drilling a separate hole causes additional trauma to the bone, and may also limit accessibility to the intended delivery location. In a third technique, the substance is delivered through the implant. This technique requires the use of a fenestrated or slotted implant.

SUMMARY

The embodiments described herein allow delivery of a substance (e.g., medication) to a fracture site after stabilization of the bone. Furthermore, the embodiments described herein allow delivery of a substance to bone through the same hole that will receive the bone implant, without requiring a separate hole to be drilled into the bone. The devices and methods described herein also allow material to be removed from the interior of a bone.

One embodiment of the invention relates to a method for delivering a substance to bone. The method includes placing a stabilizing wire in a bone and creating a hole in the bone around the stabilizing wire. A multichannel cannula is provided that includes a first channel having an open proximal end and an open distal end, the first channel being configured to receive the stabilizing wire. The multichannel cannula further includes a second channel having an inlet portal and an exit portal that are in fluid communication. The method further includes inserting the multichannel cannula into the hole in the bone such that the first channel receives the stabilizing wire, and delivering the substance into the bone by introducing the substance into the inlet portal of the second channel such that the substance exits the second channel through the exit portal.

Another embodiment of the invention relates to a method for removing material from a bone. The method includes placing a stabilizing wire in a bone and creating a hole in the bone around the stabilizing wire. A multichannel cannula is provided that includes a first channel having an open proximal end and an open distal end, the first channel being configured to receive a stabilizing wire. The multichannel cannula further includes a second channel having an inlet portal and an exit portal that are in fluid communication. The method further includes inserting the multichannel cannula into the hole in the bone such that the first channel receives the stabilizing wire. The method further includes coupling a suction device to the multichannel cannula, and removing a material from an interior of the bone by activating the suction device such that the material is drawn into the second channel through the exit portal of the second channel and the material exits the second channel through the inlet portal of the second channel.

Yet another embodiment of the invention relates to a multichannel cannula for delivering a substance to bone. The multichannel cannula includes a first channel having an open proximal end and an open distal end. The first channel is configured to receive a stabilizing wire. The multichannel cannula further includes a second channel having an inlet portal and an exit portal that are in fluid communication.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting. For example, a femur is illustrated in the drawings, but the devices and methods described herein may be used in connection with any bone in the body, including but not limited to bones in the spine, arms, hands, legs, and feet.

Figure 1:
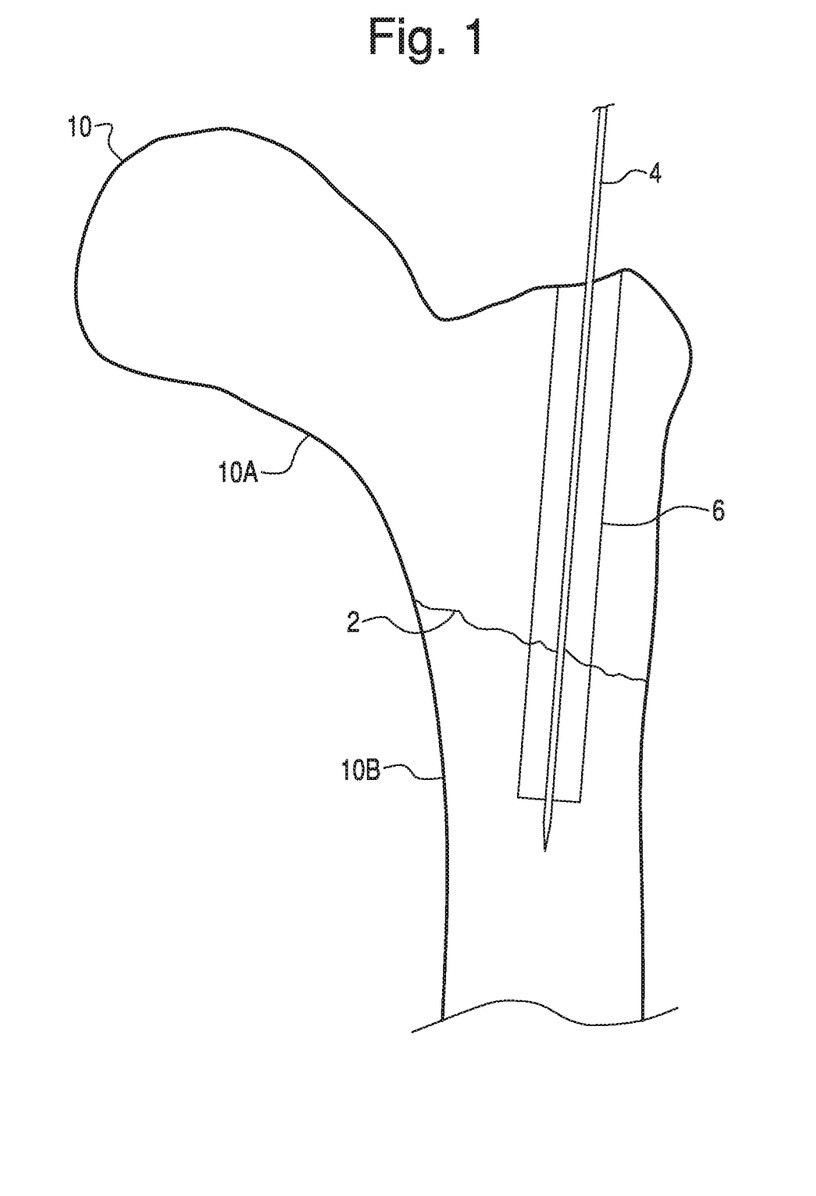
FIG. 1 illustrates a bone with a stabilizing wire and a hole in the bone around the stabilizing wire, according to an exemplary embodiment.

Referring to FIG. 1, a bone 10 includes a fracture 2. The fracture 2 separates the bone into portions 10A and 10B. In surgical procedures to repair fractured bones, a stabilizing wire 4 may be used to hold bone portions together. The stabilizing wire 4 may be any type of wire used to temporarily or permanently secure portions of bone together, such as Kirschner wires or Steinmann pins. The stabilizing wire 4 is often placed in a fractured bone 10 prior to insertion of a more permanent bone implant, such as a bone screw, nail, or other fixation structure. In addition to stabilizing the bone portions 10A and 10B, the stabilizing wire 4 may serve as a guide for a drill or bone implant. For example, the bone 10 of FIG. 1 includes a hole 6 created to eventually receive a bone implant. To create the hole 6, a cannulated drill or reamer can be used to create a hole around the stabilizing wire 4 while the tip of the stabilizing wire 4 remains fixed in bone portion 10B. The hole 6 passes through the fracture 2. A bone implant to further secure bone portions 10A and 10B together can then be guided over stabilizing wire 4 and into the hole 6.

Figure 8:
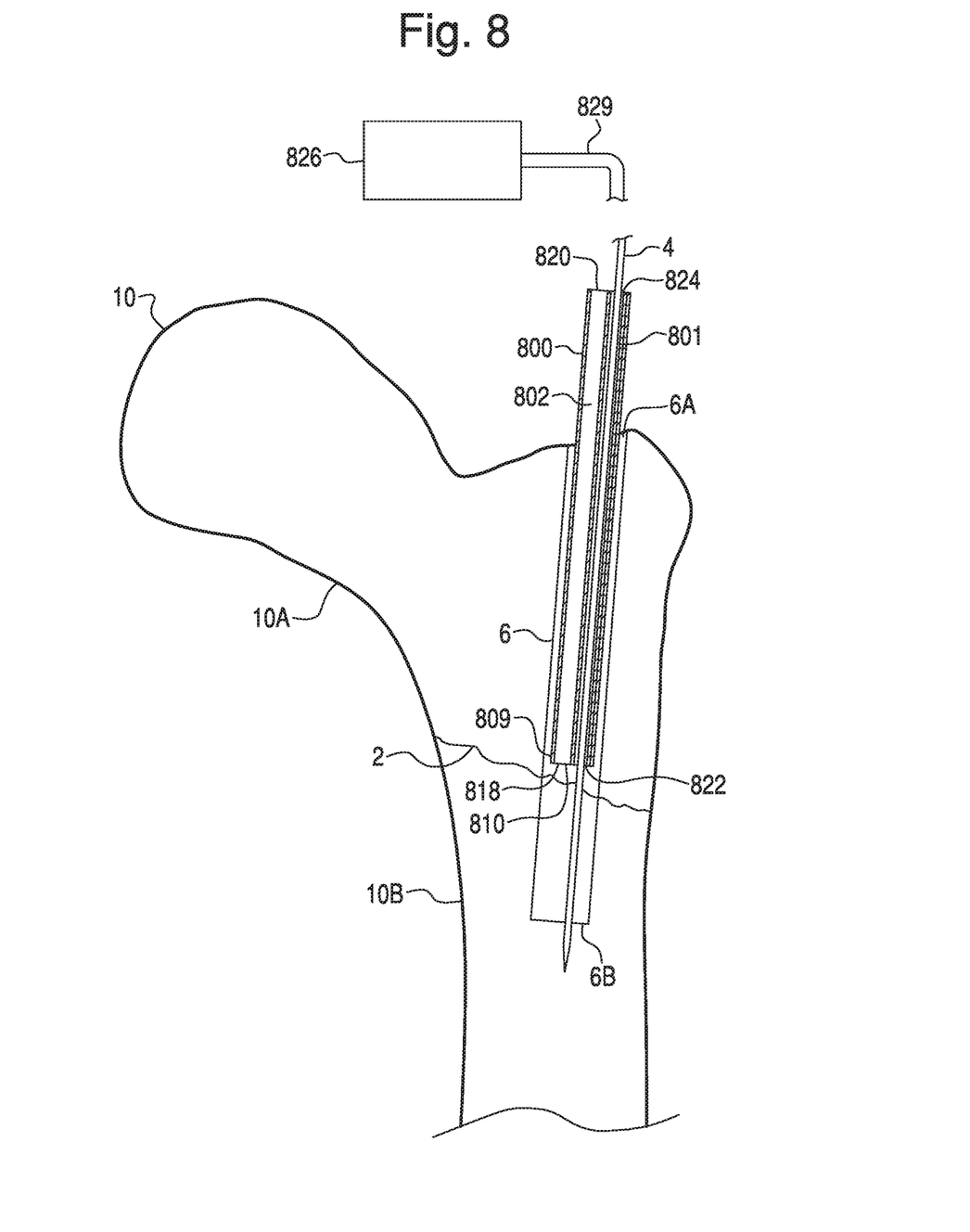
FIG. 8 illustrates the bone and stabilizing wire shown in FIG. 1 with a multichannel cannula introduced over the stabilizing wire, according to an exemplary embodiment.

Referring to FIG. 8, according to an exemplary embodiment, a multichannel cannula 800 having two or more channels may be introduced over the stabilizing wire 4 to deliver substances to the interior of bone 10. In one embodiment, the multichannel cannula is introduced over the stabilizing wire 4 after creation of hole 6, but prior to placement of a bone implant into the hole 6. A first channel of the multichannel cannula receives the stabilizing wire 4. The other channels of the multichannel cannula may be used for delivering substances to the interior of bone 10, as described in more detail below. The substance delivered using the multichannel cannulas described herein may be any type of substance a user desires to deliver to the interior of a bone, including medication such as calcium phosphate paste, an antibiotic, or a chemotherapeutic agent.

Figure 6:
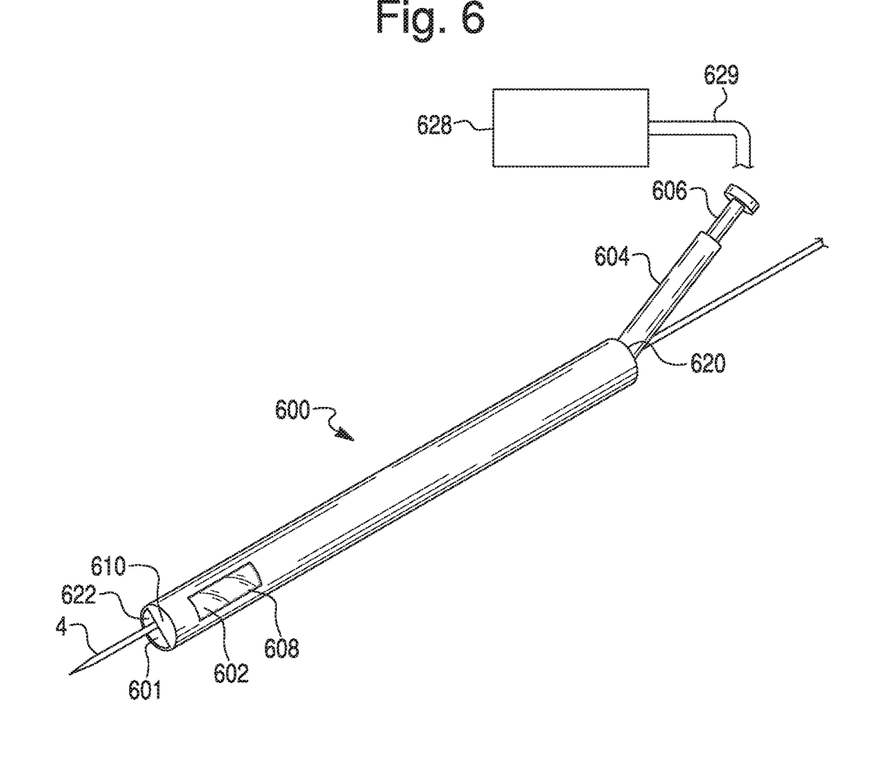
FIG. 6 illustrates a multichannel cannula having a side port and a delivery portal, according to an exemplary embodiment.
Figure 7:
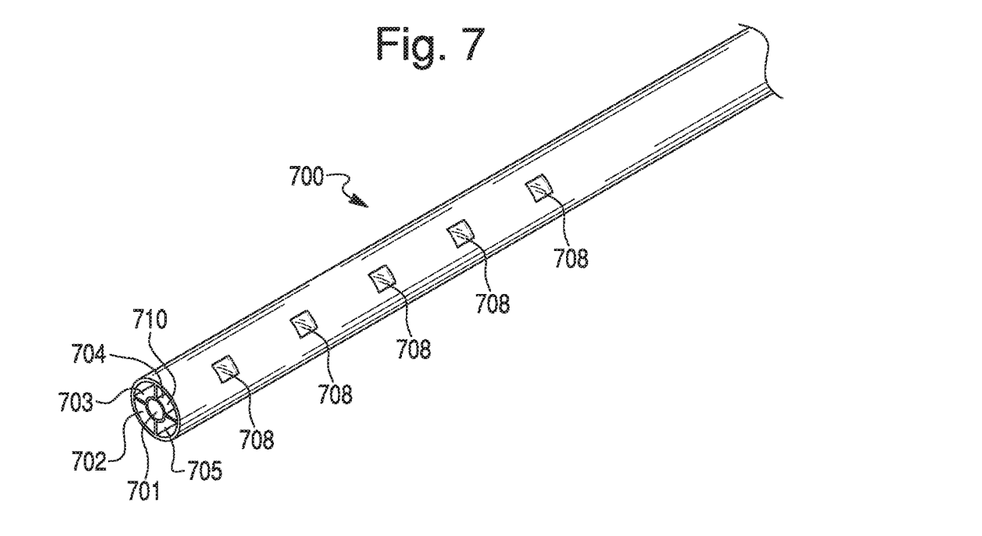
FIG. 7 illustrates a multichannel cannula with a plurality of exit portals, including open distal ends of channels and multiple side ports, according to an exemplary embodiment.

The multichannel cannulas described herein are substantially elongated structures with two or more channels, as can be seen in FIGS. 6-8 (reference numbers 600, 700, and 800, respectively). The multichannel cannulas described herein include a first channel having an open proximal end (e.g., 824 shown in FIG. 8) and an open distal end (e.g., 822 shown in FIG. 8). The open proximal end and open distal end allow the first channel to be threaded over a stabilizing wire 4. Thus, the first channel is configured to receive a stabilizing wire 4. In one embodiment, the first channel is substantially cylindrical and has a diameter slightly larger than the diameter of the stabilizing wire. The side wall of the cylindrical first channel (as distinguished from the open ends of the first channel) may be continuous, meaning there are no open portals or other openings along the side wall of the first channel. In one embodiment, liquid cannot penetrate the side wall of the first channel.

The multichannel cannulas described herein further include a second channel (e.g., 802 shown in FIG. 8). The second channel includes at least one inlet portal (e.g., 820 shown in FIG. 8) and at least one exit portal (e.g., open distal end 810 shown in FIG. 8; side exit portals 708 shown in FIG. 7). In some methods described herein, the inlet portal of the second channel serves as an inlet for a substance to be delivered to the interior of a bone. In these embodiments, the exit portal of the second channel serves as an outlet for the substance. In other methods of using a multichannel cannula, the exit portal of the second channel serves as an inlet for material being drawn into the second channel and removed from the interior of a bone. In these embodiments, the inlet portal of the second channel serves out an outlet for this removed material. The inlet portal and exit portal of the second channel are thus in fluid communication to allow substances or materials to be delivered to or removed from the interior of a bone.

FIGS. 2-5 illustrate cross-sectional views of various embodiments of multichannel cannulas. The multichannel cannulas shown in FIGS. 2-5 each include at least two interior channels. The channels of a multichannel cannula may be structured in a variety of ways to enhance a user's ability to precisely deliver a substance to an intended location within a bone.

Figure 2:
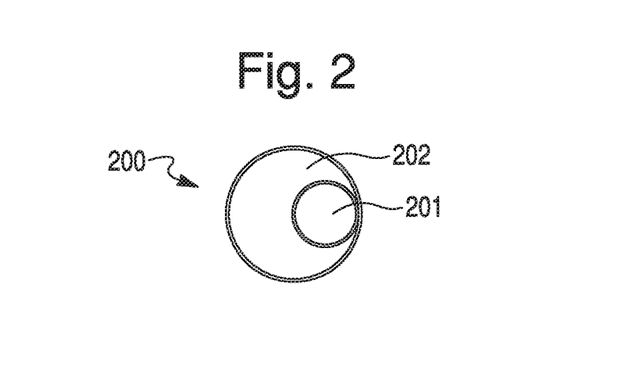
FIGS. 2-5 illustrate cross-sectional views of various exemplary embodiments of a multichannel cannula.

The multichannel cannula 200 shown in FIG. 2 includes a first channel 201 and a second channel 202. In this embodiment, first channel 201 is smaller than second channel 202, and first channel 201 is contained within the bounds of second channel 202. The cross-section of multichannel cannula 200 is substantially circular. In one embodiment, channel 201 receives a stabilizing wire 4 during a surgical procedure.

Figure 3:
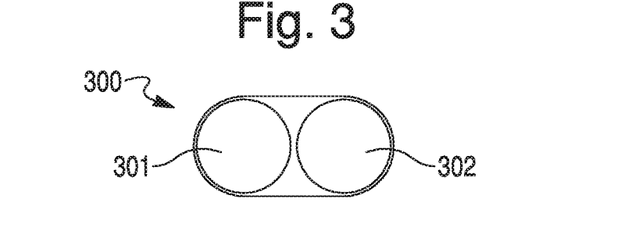

The multichannel cannula 300 shown in FIG. 3 also includes two channels—first channel 301 and second channel 302. In the embodiment of FIG. 3, first channel 301 and second channel 302 have substantially circular cross-sections and have approximately the same diameter. Furthermore, first channel 301 and second channel 302 are arranged next to each other such that the multichannel cannula 300 has a substantially ovular cross-section. During use of the multichannel cannula 300 of FIG. 3, either first channel 301 or second channel 302 may receive a stabilizing wire 4.

Figure 4:
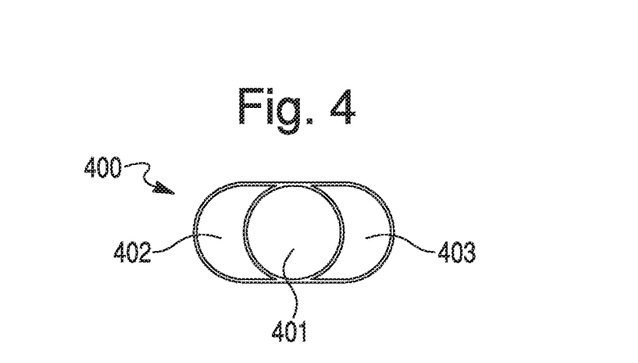

Referring to FIG. 4, multichannel cannula 400 includes a first channel 401, a second channel 402, and a third channel 403. The first channel 401 has a substantially circular cross-section, while second channel 402 and third channel 403 have crescent-shaped cross-sections. Second channel 402 and third channel 403 are arranged on either side of first channel 401 such that multichannel cannula 400 has a substantially ovular cross-section. In one embodiment, first channel 401 receives a stabilizing wire 4 during a surgical procedure.

Figure 5:
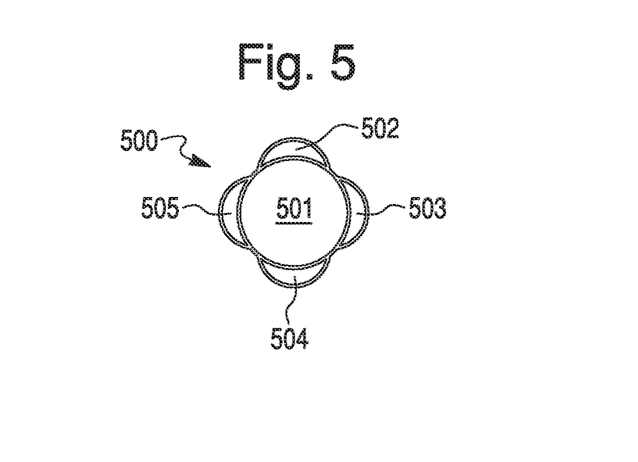

Multichannel cannula 500, shown in FIG. 5, includes five separate channels. The cross-section of first channel 501 is substantially circular. Second channel 502, third channel 503, fourth channel 504, and fifth channel 505 have crescent-shaped cross-sections and are arranged around first channel 501. The cross-sectional shape of multichannel cannula 500 is thus an irregular shape, as illustrated in FIG. 5. In one embodiment, first channel 501 receives a stabilizing wire 4 during a surgical procedure.

The multichannel cannulas described herein can be made of any material suitable for placement into a bone without harmful effects on the patient. In one embodiment, the multichannel cannula is made of stainless steel or other type of metal. In another embodiment, the multichannel cannula is made of a rigid plastic, such as polyethylketone, that cannot be easily bent or manipulated into alternative configurations. A rigid cannula may be advantageous to provide stability when introducing the cannula into a hole 4 in a bone 10. Furthermore, a rigid cannula provides stability for various procedures that a more flexible multichannel cannula may not provide. For example, if a surgeon desires to use a plunger or other device to push a substance from the multichannel cannula and into the bone, a rigid cannula may be more desirable. As another example, a rigid cannula is able to withstand more significant forces than a flexible cannula (e.g., forces applied to the cannula by a delivery device 628 or a suction device 826, and the forces resulting from movement of substances through the channels and through any open portals in the cannula).

FIG. 6 provides a perspective view of another embodiment of a multichannel cannula. Multichannel cannula 600 includes a first channel 601, a second channel 602, a delivery portal 604, and a side exit portal 608. The multichannel cannula 600 is threaded over a stabilizing wire 4, such as stabilizing wire 4 in bone 10 (as shown in FIG. 8). The stabilizing wire therefore lies within the first channel 601. The delivery portal 604 is coupled to an inlet portal 620 of the second channel 602 such that a substance can flow from the delivery portal 604, through the inlet portal 620, and into the second channel 602. The delivery portal 604 may be angled relative to the multichannel cannula 600, as shown in FIG. 6. In an alternative embodiment, the longitudinal axis of the delivery portal 604 is aligned parallel to the longitudinal axis of the multichannel cannula 600.

Various delivery devices can be coupled to the delivery portal 604 to assist in delivering substances to the second channel 602 of multichannel cannula 600. The delivery portal 604 may include a removable plug 606. In one embodiment, a user removes plug 606 to couple a delivery device 628 (illustrated schematically in FIG. 6) to delivery portal 604. The delivery device 628 may include a syringe, a pump, or a reservoir. Tubing 629 may be used to connect the delivery device 628 to the delivery portal 604. The type of delivery device selected by a user may depend on the type of substance to be delivered to the bone.

Once a substance has been delivered to second channel 602 of the multichannel cannula 600 through the inlet portal 620, the substance exits second channel 602 via a side exit portal 608 located on an outer wall of the second channel 602. In this embodiment, the distal end 610 of second channel 602 is closed, preventing the substance from exiting the distal end 610 of the second channel 602. However, in an alternative embodiment, the distal end 610 of the second channel 602 may be open to create an exit portal such that the substance can exit the second channel 602 through both the side exit portal 608 and the open distal end 610. During use of multichannel cannula 600, a user can align the side exit portal 608 with the area of the bone to be treated with the substance.

Referring to FIG. 7, multichannel cannula 700 includes five channels (701-705), each with an open distal end that can serve as an exit portal for substance delivery. In this embodiment, the fourth channel 704 includes a plurality of side exit portals 708, although any of the other channels 702-705 may include one or more side exit portals. The first channel 701 is configured to receive stabilizing wire 4 during a surgical procedure. A substance can be delivered to the inlet portals of any of channels 702-705 via a delivery portal, such as the delivery portal 604 described in connection with FIG. 6. In one embodiment, the substance is delivered to fourth channel 704. The substance then travels through fourth channel 704, exiting through side exit portals 708 and the exit portal created by the open distal end 710 of the fourth channel 704. In an alternative embodiment, the distal end 710 of fourth channel 704 is closed to prevent substance from exiting the distal end 710. The multiple exit portals 708, 710 in the embodiment of FIG. 7 allow the substance to be delivered to multiple areas within the interior of a bone. For example, the open distal end 710 may deliver the substance to a distal end of a hole 6 in a bone (e.g., in bone 10 shown in FIG. 8) while the exit portals 708 deliver the substance to one or more fracture sites 2.

FIG. 8 illustrates a multichannel cannula 800 placed within bone 10 for substance delivery. The multichannel cannula 800 illustrated in FIG. 8 includes at least a first channel 801 and a second channel 802. First channel 801 is shown threaded over stabilizing wire 4. Second channel 802 is therefore used for substance delivery or to remove material from the interior of a bone. Any of the embodiments of multichannel cannulas described herein (e.g., 200, 300, 400, 500, 600, 700, and 900), and any combination of the features of these embodiments, may be utilized in the manner shown in FIG. 8 to either deliver a substance to bone or remove material from the interior of a bone. Thus, references and disclosures related to methods for using multichannel cannula 800 are to be understood to be references and disclosures related to methods for using any of the other structural embodiments of multichannel cannulas described herein.

One method of delivering a substance to bone according to an exemplary embodiment includes placing stabilizing wire 4 into bone 10 and creating a hole 6 in the bone 10 around the stabilizing wire 4, as described above. The method further includes providing a multichannel cannula 800 having a first channel 801 with an open proximal end 824 and an open distal end 822. As also described above, the proximal end 824 and distal end 822 of the first channel 801 are open so that the first channel 801 can receive the stabilizing wire 4. The multichannel cannula 800 further includes a second channel 802 having an inlet portal 820 and an exit portal 818 that are in fluid communication.

The multichannel cannula 800 may be inserted into the hole 6 in the bone 10 such that the first channel 801 receives the stabilizing wire 4. During the step of inserting the multichannel cannula 800 into the hole 6, the multichannel cannula 800 can be inserted into the proximal end 6A of hole 6 to any desired depth. A substance is then delivered to the interior of bone 10 by introducing the substance into the inlet portal 820 of the second channel 802 such that the substance exits the second channel 802 through the exit portal 818 (i.e., the open distal end 810 of second channel 802). In one embodiment, the multichannel cannula 800 is inserted into hole 6 such that the distal end 809 of the multichannel cannula 800 is near fracture 2. The substance can therefore be delivered to the fracture site through the open distal end 810 of the second channel 802. In another embodiment, the multichannel cannula 800 is inserted farther into hole 6 such that substance is delivered through the open distal end 810 of the second channel 802 closer to the distal end 6B of hole 6.

A user may select a multichannel cannula having a particular configuration and number of exit portals depending on a patient's bone fracture. For example, some types of fractures may be most easily treated by delivering a substance to a location that can be aligned with a distal end of a multichannel cannula. In this scenario, a user may select a multichannel cannula 800 in which the distal end 810 of a second channel 802 is open such that the substance can be delivered to bone 10 through this open distal end 810. In connection with other types of fractures, the user may desire to treat the bone 10 by delivering medication to one or more locations along the periphery of a hole 6 in the bone 10. Thus, a user may select a multichannel cannula 800 in which distal end 810 of second channel 802 is closed, and a substance is delivered to the bone through side exit portals such as those described in connection with FIGS. 6 and 7. In yet another embodiment, a substance may be delivered to bone 10 through a channel in multichannel cannula 800 having both an open distal end 810 and one or more side exit portals.

The multichannel cannula 800 may also be used during treatment of a patient with a weakened, but unfractured bone. A patient's bone can be weakened due to osteoporosis, metastasis of a cancer, or other disease that causes bone deterioration. A surgeon may be able to analyze the state of the patient's bone and determine areas that are likely to sustain a fracture in the future. To treat the weakened bone, a stabilizing pin 4 is inserted and a hole is drilled into the bone. The multichannel cannula 800 is then threaded over the stabilizing pin 4. A cement (e.g., calcium phosphate paste, methylmethacrylate) is injected through a channel of the multichannel cannula 800. The cement penetrates the surrounding bone and strengthens the area. After removal of the multichannel cannula 800, the hole in the bone may be filled with cement or a bone implant.

Prior to or during substance delivery, a user may rotate the multichannel cannula 800 around the stabilizing wire 4. Rotating the multichannel cannula 800 may help a user align an exit portal with an intended delivery location within the bone in order to direct substance delivery to the intended delivery location. Furthermore, the ability to rotate the multichannel cannula 800 around a stabilizing wire 4 may help during guidance of the multichannel cannula 800 proximally and distally within hole 6.

Fluoroscopic guidance may increase a user's ability to precisely deliver a substance to a desired location within bone 10. The ability to view the multichannel cannula 800 during insertion allows a user to adjust the position of multichannel cannula 800 to precisely align any exit portals of the multichannel cannula 800 with the intended delivery sites within bone 10. Once the multichannel cannula 800 is positioned and substance delivery has begun, the user can use fluoroscopic guidance to determine whether any adjustments to the position of the multichannel cannula 800 should be made to more precisely deliver the substance. For example, based on fluoroscopic guidance, the user may determine that the multichannel cannula 800 should be inserted farther into hole 6. As another example, the image guidance may indicate that multichannel cannula 800 should be rotated about stabilizing wire 4 to increase delivery accuracy.

The multichannel cannulas described herein may include radiopaque markers to facilitate image guidance. The radiopaque markers may be located on or near the distal tip of the multichannel cannula. In one embodiment, separate radiopaque markers are provided near the distal opening of multiple channels of the multichannel cannula. Radiopaque markers may also be provided near side portal openings in the cannula. The radiopaque markers assist a user in accurately positioning the multichannel cannula during a surgical procedure to deliver or remove a substance from a bone. Furthermore, the markers allow a user to see where a substance is exiting or entering the multichannel cannula.

Figure 9:
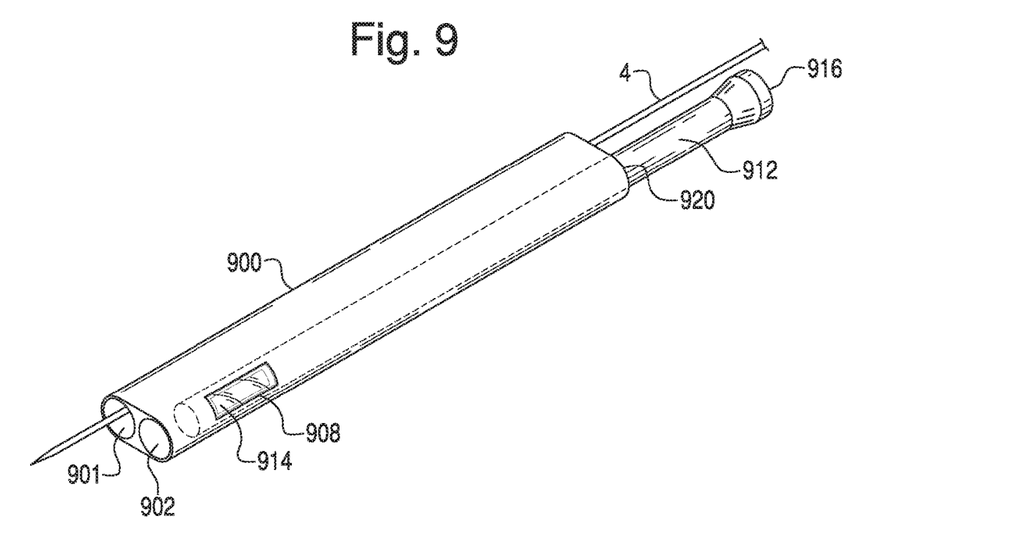
FIG. 9 illustrates a multichannel cannula with a stabilizing wire within a first channel and a delivery insert within a second channel.

Referring to FIG. 9, a multichannel cannula 900 in accordance with another exemplary embodiment includes a first channel 901 and a second channel 902. The second channel 902 includes a side exit portal 908 for the substance to exit the second channel 902. In the embodiment of FIG. 9, an insert 912 having an exit portal 914 is used in combination with multichannel cannula 900 to deliver a substance to bone. In an alternative embodiment, the insert 912 includes multiple side exit portals (not shown). The insert 912 may be one of the embodiments of inserts described in U.S. patent application Ser. No. 13/270,072, titled "Method and Device for Delivering Medicine to Bone," filed Oct. 10, 2011, and hereby incorporated by reference herein in its entirety. In use, the insert 912 is inserted into the second channel 902. A substance is then introduced into the proximal end 916 of the insert 912. The substance then exits the exit portal 914 of the insert and the exit portal 908 of the second channel 902 of the multichannel cannula 900. The insert 912 can be adjusted within second channel 902 to alter the amount of substance ultimately delivered through side exit portal 908 of the multichannel cannula 900. For example, the insert 912 may be pulled in a proximal direction (i.e., away from the multichannel cannula 900) such that only a portion of side exit portal 914 is aligned with side exit portal 908. Alternatively, the insert 912 can be pushed in a distal direction to fully align side exit portal 914 with side exit portal 908, as shown in FIG. 9, which maximizes the amount of the substance delivered through side exit portal 908. The insert 912 may also be rotated around its longitudinal axis to alter the alignment of side exit portal 914 of the insert 912 and side exit portal 908 of the multichannel cannula 900, thus adjusting the amount of the substance delivered. A delivery device 628 (shown schematically in FIG. 6), such as a syringe, a pump, or a reservoir, may be attached to the proximal end 916 of the insert 912.

In another exemplary method, any of the multichannel cannulas described herein may be used to remove material, such as bone marrow or blood, from the interior of a bone 10. Referring to FIG. 8, a suction device 826 may be coupled to the proximal end of multichannel cannula 800 to aid in the removal of material. In one embodiment, the suction device 826 is coupled to the proximal end of second channel 802 by tubing 829 or via a delivery portal (e.g., the delivery portal 604 shown in FIG. 6). Upon activating the suction device 826, material being removed from the bone 10 travels through the multichannel cannula 800 in an opposite manner from the embodiments in which a substance is being delivered to the bone through multichannel cannula 800. For example, in the embodiment shown in FIG. 8, activation of suction device 826 causes material to enter the multichannel cannula 800 through the exit portal created by open distal end 810 or through any side exit portals in the multichannel cannula 800. The material then travels through second channel 802 and exits the multichannel cannula 800 through the inlet portal 820 at the proximal end of the second channel 802. The exit portals of the multichannel cannula 800 may be aligned within bone 10 to remove material from intended locations near the exit portals.

A user may use the multichannel cannula 800 to both deliver substances to bone 10 and remove materials from the interior of a bone 10 during the same surgical procedure. In one embodiment, a user first uses the multichannel cannula 800 to remove material from the interior of the bone 10. Next, the multichannel cannula 800 is used to deliver substances to areas within the bone 10. Alternatively, a user may first deliver a substance to the interior of bone 10 using the multichannel cannula 800. After substance delivery, the user may remove excess substance (e.g., medication) or other materials (e.g., blood) by utilizing a suction device 826 coupled to the proximal end of the multichannel cannula 800. The combination of a multichannel cannula and an insert, such as the multichannel cannula 900 and insert 912 shown in FIG. 9, may similarly be used in connection with a suction device 826 to remove material from the interior of a bone 10. In this embodiment, the suction device 826 can be coupled via tubing or via a delivery portal (e.g., the delivery portal 604 shown in FIG. 6) to the proximal end 916 of the insert 912.

The multichannel cannulas described herein can be used to irrigate the interior of a bone by simultaneously delivering a substance to the bone 10 using one channel and applying a suction force to a separate channel. Irrigation may be useful for reducing the risk of infection or contamination within a bone. In one embodiment, a solution containing antibiotics or other medication is introduced into a first channel of a multichannel cannula. The solution travels through the first channel and enters the interior of a bone through one or more exit portals of the first channel. Simultaneously or shortly thereafter, a suction force is applied to a second channel of the multichannel cannula using a suction device, such as suction device 826 shown in FIG. 8. The suction draws the solution from the interior of the bone and back into the multichannel cannula through an open portal of the second channel. In this manner, the interior of the bone can be irrigated using a multichannel cannula. The channel used to deliver the substance to the bone may or may not contain a stabilizing wire 4. Similarly, the channel used to draw the substance back out of the bone may or may not contain a stabilizing wire 4. In other words, the presence of a stabilizing wire 4 within a channel does not prevent substances from flowing through the channel.

The various multichannel cannula embodiments can be used in surgical procedures other than in connection with delivering or removing substances from bone. For example, the multichannel cannulas can be used in procedures requiring insertion of a cannula into a vessel. In this embodiment, a guidewire is inserted into the patient's vessel, and a first channel of the multichannel cannula is then threaded over the guidewire. The cannula can then be used as described in connection with the various methods disclosed herein to deliver or remove a substance from the vessel through a channel of the cannula. In another embodiment, the multichannel cannula is used in ear, nose, and throat procedures, with or without the use of a guidewire.

The construction and arrangement of the devices and methods as shown in the various exemplary embodiments are illustrative only. Although only a few embodiments have been described in detail in this disclosure, many modifications are possible (e.g., variations in sizes, dimensions, structures, shapes and proportions of the various elements, use of materials, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A method for delivering a substance to bone, comprising:
    placing a stabilizing wire in a bone;
    creating a hole in the bone around the stabilizing wire;
    providing a multichannel cannula, comprising:
        a first channel having an open proximal end and an open distal end, wherein the first channel is configured to receive the stabilizing wire; and
        a second channel having an inlet portal and an exit portal, wherein the inlet portal and the exit portal are in fluid communication for continuous flow of the substance from the inlet portal to the exit portal;
    inserting the multichannel cannula into the hole in the bone such that the first channel receives the stabilizing wire; and
    delivering the substance into the bone by introducing the substance into the inlet portal of the second channel such that the substance flows continuously in the second channel between the inlet portal and the exit portal, wherein the stabilizing wire remains placed in the bone and received by the first channel during delivery of the substance to the bone.

2. The method of claim 1, wherein the first channel is substantially cylindrical, and a side wall of the cylindrical first channel is continuous such that no open portals are formed in the side wall.

3. The method of claim 1, wherein the exit portal of the second channel is an open distal end of the second channel.

4. The method of claim 1,
    wherein the exit portal of the second channel is a side exit portal on an outer wall of the second channel, and
    wherein a distal end of the second channel is closed such that the substance is prevented from exiting the distal end of the second channel.

5. The method of claim 1, wherein the second channel includes a plurality of exit portals.

6. The method of claim 1, wherein the multichannel cannula comprises three, four, or five channels.

7. The method of claim 1, wherein the multichannel cannula further comprises a delivery portal coupled to the inlet portal of the second channel, wherein the delivery portal is configured to be coupled to a delivery device.

8. The method of claim 1, further comprising the step of rotating the multichannel cannula around the stabilizing wire to align the exit portal with an intended delivery location within the bone.

9. The method of claim 1, wherein a user employs fluoroscopic guidance during the step of inserting the multichannel cannula into the hole in the bone.

10. The method of claim 1,
    further comprising the step of inserting an insert having an exit portal into the second channel of the multichannel cannula;
    wherein the step of delivering the substance into the bone includes introducing the substance into the insert such that the substance exits the exit portal of the second channel via the exit portal of the insert; and
    wherein the insert is adjustable within the second channel to alter the amount of substance delivered to the bone through the exit portal of the second channel.

11. A method for removing material from a bone, comprising:
    placing a stabilizing wire in a bone;
    creating a hole in the bone around the stabilizing wire;
    providing a multichannel cannula comprising:
        a first channel having an open proximal end and an open distal end, wherein the first channel is configured to receive a stabilizing wire; and
        a second channel having an inlet portal and an exit portal, wherein the inlet portal and the exit portal are in fluid communication for continuous flow of the substance between the inlet portal and the exit portal;
    inserting the multichannel cannula into the hole in the bone such that the first channel receives the stabilizing wire;
    coupling a suction device to the multichannel cannula; and
    removing a material from an interior of the bone by activating the suction device such that the material is drawn into the second channel through the exit portal of the second channel, flows continuously in the second channel between the exit portal and the inlet portal, and exits the second channel through the inlet portal of the second channel, wherein the stabilizing wire remains placed in the bone and received by the first channel during removal of the material from the bone.

* * * * *